United States Patent [19]
Phillips et al.

[11] Patent Number: 5,220,919
[45] Date of Patent: Jun. 22, 1993

[54] BLOOD ALCOHOL MONITOR

[75] Inventors: Mary F. Phillips, Lakewood; Jeffrey S. Hawthorne, Aurora, both of Colo.

[73] Assignee: Safety Technology Partners, Ltd., Denver, Colo.

[21] Appl. No.: 748,976

[22] Filed: Aug. 23, 1991

[51] Int. Cl.$^5$ ............................................. A61B 5/00
[52] U.S. Cl. ..................................... 128/632; 128/635; 128/903; 436/68; 436/132; 340/573
[58] Field of Search ............... 128/632, 635, 640, 903; 436/68, 132; 204/403, 402; 340/573

[56] References Cited

U.S. PATENT DOCUMENTS

| 3,649,199 | 3/1972 | Littlejohn | 128/632 |
| 3,940,251 | 2/1976 | Jones et al. | 23/254 |
| 4,401,122 | 8/1983 | Clark, Jr. | 128/635 |
| 4,539,994 | 9/1985 | Baumbach et al. | 128/635 |
| 4,665,385 | 5/1987 | Henderson | 340/539 |
| 4,809,698 | 3/1989 | Kogo | 128/632 |
| 4,843,377 | 6/1989 | Fuller et al. | 340/573 |
| 4,916,435 | 4/1990 | Fuller | 340/573 |
| 4,996,161 | 2/1991 | Conners et al. | 340/573 |
| 4,997,770 | 3/1991 | Giles et al. | 436/132 |

Primary Examiner—Lee S. Cohen
Assistant Examiner—Brian L. Casler
Attorney, Agent, or Firm—John E. Reilly

[57] ABSTRACT

A device which measures ethanol levels expelled through a subject's skin to monitor blood alcohol level at regular or random intervals. The device differentiates between a positive reading caused by an external, interferant, source of ethanol and a positive reading caused by consumption of alcohol. The device is attached to the subject by a secure conductive strap which provides an indication that the device remains attached to the subject. The device monitors the skin temperature of the subject prior to performing the alcohol test to provide an indication of a barrier being placed between the device and the subject's skin. The device measures the distance from the subject's skin, thereby preventing the subject from moving the device far enough away to provide an inaccurate indication of the amount of alcohol in the subject's blood and providing another tamper indication if the device is removed.

27 Claims, 10 Drawing Sheets

BLOOD ALCOHOL MONITOR

FIELD OF THE INVENTION

This invention relates to continuous monitoring of human blood alcohol levels and more particularly to a non-invasive blood alcohol level monitoring device. Even more particularly, the invention relates to a portable device, affixed to the subject, for monitoring blood alcohol, without requiring subject participation, by determining the alcohol levels expelled through a subject's skin.

BACKGROUND OF THE INVENTION

Devices for testing the blood and breath alcohol content of a human subject have been used for many years. This type of testing is typically done using breath alcohol testing methods, for example, see U.S. Pat. No. 3,940,251, entitled "Apparatus for Detecting or Measuring a Constituent of a Gas", issued Feb. 24, 1976 to Jones, et al. This system tests the alcohol content of a subject's breath by utilizing a breath analyzing sensor in a breath sampling system that includes a disposable tube. A subject exhales into the tube and an operator of the handheld instrument pushes a button releasing a spring loaded pump which draws a deep lung breath sample into the device. The breath sample is then analyzed by a sensor and the subsequent reading is interpreted by the operator.

More recently such breath alcohol testing instruments have been added to Home Arrest Systems. These systems have an encoded transmitter and a base receiver unit. The transmitter is attached to the subject, and the system determines if the subject is located within a short distance, usually under 250 feet, from the base receiver unit. These systems may attach a conventional breath alcohol testing device to the base unit.

Other prior art, for example U.S. Pat. No. 4,843,377 issued Jun. 27, 1989 to Fuller et al., and U.S. Pat. No. 4,916,435 issued Apr. 10, 1990 to Fuller, consists of a one way video system with an attached conventional breath alcohol tester. This system transmits a picture of the test results, along with a picture of the subject taking the test, over conventional phone lines to a central monitoring station. An operator at the central station must view the video picture to help assure that the proper subject is taking the breath alcohol test. U.S. Pat. No. 4,665,385 entitled "Hazardous Condition Monitoring System", issued May 12, 1987 to Henderson consists of a hazardous gas sensor and an ethanol sensor located near a microphone attached to a walkie talkie. The system transmits encoded information pertaining to hazardous gas levels and subject breath alcohol levels when the walkie talkie is used.

U.S. Pat. No. 4,997,770 entitled "Method and Means for Detecting Blood Alcohol in Humans by Testing Vapor above the Eye", issued Mar. 5, 1991 to Giles, et al., measures the blood alcohol content of vapors emitted by the human eye. This device requires that a cup be placed over the subject's eye, and a separate analyzer measures the alcohol content of gases collected in the cup.

All the prior art described above requires the full cooperation of the subject to complete a successful breath test. Except for the system of Henderson, none of the remote alcohol systems described above are portable. Also, except for Giles et al., all the prior art described above measures breath alcohol content.

Alcohol monitoring systems are currently needed to periodically measure a subject's blood alcohol level at a remote location over an extended period of time, such as when a subject is in an alcohol rehabilitation program, or is under court order to not consume alcohol. For this type of system, identification of the subject providing the breath sample is a very significant problem. For example, an unsupervised remote breath alcohol tester being used by the subject is ineffective if an operator is not available to identify that the correct subject is breathing into the instrument. Because of the requirement of subject identification, these systems typically require the active participation and cooperation of the subject. Sometimes the subjects are uncooperative and will go to great lengths to avoid the testing. This increases the time and effort necessary to perform the testing, which often results in less testing being performed.

Another problem is that once a subject has been tested, the subject knows they will not be tested again for some period of time, such as when the subject is involved in a work release or outpatient alcohol rehabilitation program. This allows the subject to leave the location of the stationary remote alcohol breath tester unit and immediately consume alcohol at high levels just after the testing. The subject is unlikely to show a high level of alcohol content if tested at a much later time because the rate of dissipation of alcohol from the human body is quite high.

Another major problem of all of these systems is the lack of any effective means to determine if a positive reading is created by ethanol in the testing subject's breath or blood, or by tampering with the instrument, such as, by pouring alcohol over the sensor in an effort to discredit the instrument. A wide variety of common interferant gases will react with the sensors utilized in the systems in a manner very similar to ethanol, which may provide a false positive reading and it is important to be able to screen out interferant gases. For a subject in an alcohol treatment program, a false reading may have severe consequences.

There is need in the art then for an apparatus and method to passively test the blood alcohol content of a human subject. There is further need for such a system to passively confirm the identity of the subject during such testing. Still another need in the art is for such a system to perform such testing automatically without the need of an operator, and without the need for cooperation from the subject being tested. A further need in the art is for such a system to perform frequent testing at either predetermined times, or at random times, and to perform such testing at any arbitrary location Another important need unanswered by prior art is a means of determining if a reading indicating the subject has consumed alcohol is caused by the blood alcohol levels of the subject or by numerous interferant gases which react with sensors in a manner similar to alcohol The present invention satisfies these and other needs.

SUMMARY OF THE INVENTION

It is an aspect of the present invention to perform testing which indicates the blood alcohol content of a human subject.

It is another aspect of the invention to passively confirm the identity of the subject during such testing.

Another aspect of the invention is to perform such testing in a passive manner without requiring cooperation from the subject.

Yet another aspect is to perform such testing automatically without requiring an operator.

Still another aspect of the invention is to perform continuous testing at predetermined times, typically every one-half hour, or to perform such testing at random times, regardless of the location of the subject and without the subject's knowledge that the test is being performed.

A further aspect of the invention is to perform such testing at any arbitrary location.

A still further aspect of this invention is to provide a means of determining whether output from the ethanol sensor is caused by the subject's blood alcohol levels or an interferant gas reacting with the ethanol sensor.

A still further aspect of the invention is to provide a means of reprogramming the invention from a remote location.

The above and other aspects of the invention are accomplished in a small, portable system that is attached to the subject by a secure, monitored strap. The system provides for the continuous monitoring of a subject's blood alcohol level by measuring the level of ethanol that has been expelled through the subject's skin. The system determines the subject's blood alcohol level by measuring the amount of ethanol at a predetermined distance away from the subject's skin, which provides an indication of the relative amount of ethanol in the subject's blood. The system also monitors the skin temperature of the subject prior to performing the alcohol test, thus providing an indication that a barrier has not been placed between the device and the subject's skin and to further confirm the device has not been removed from the subject. Furthermore, the device uses a distance measuring system to measure the distance of the device from the subject's skin, to further confirm that the system has not been removed from the subject or that a barrier has not been placed between the subject's skin and the unit.

Typically, the device can be attached to a subject's arm or leg to provide periodic monitoring of the subject's blood alcohol content. The device cannot be removed by the subject, therefore, once attached, the device provides passive confirmation of the identification of the subject. If the subject attempts to remove the device, the device will detect such removal and provide an error indication. Because the device is small and portable, it is attached directly to the subject wherever the subject is located, thus, the measurement can be performed at any location, and at any time, 24-hours a day, seven days a week.

The system contains a timer which allows the device to perform periodic blood alcohol measurements, typically every 30 minutes. The device can also be set to perform measurements at random times. The device performs such testing automatically, and requires no human operator's assistance or subject assistance to perform the measurements. Furthermore, the subject is unaware when a measurement is being taken, and is also unaware of the amount of alcohol measured by the device.

Periodically, the subject connects the device to a base unit, which automatically transmits the positive, stored readings taken, device tamper error indications, and system diagnostic error indications, and the total number of tests performed, to a remote monitoring system. Typically this connection is made once daily, however, the device is capable of storing readings for a period of over 30 days.

BRIEF DESCRIPTION OF THE DRAWINGS

The above and other aspects, features, and advantages of the invention will be better understood by reading the following more particular description of the invention, presented in conjunction with the following drawings, wherein.

DESCRIPTION OF THE PREFERRED EMBODIMENT

The following description is of the best presently contemplated mode of carrying out the present invention. This description is not to be taken in a limiting sense but is made merely for the purpose of describing the general principles of the invention. The scope of the invention should be determined by referencing the appended claims.

Figure 1:
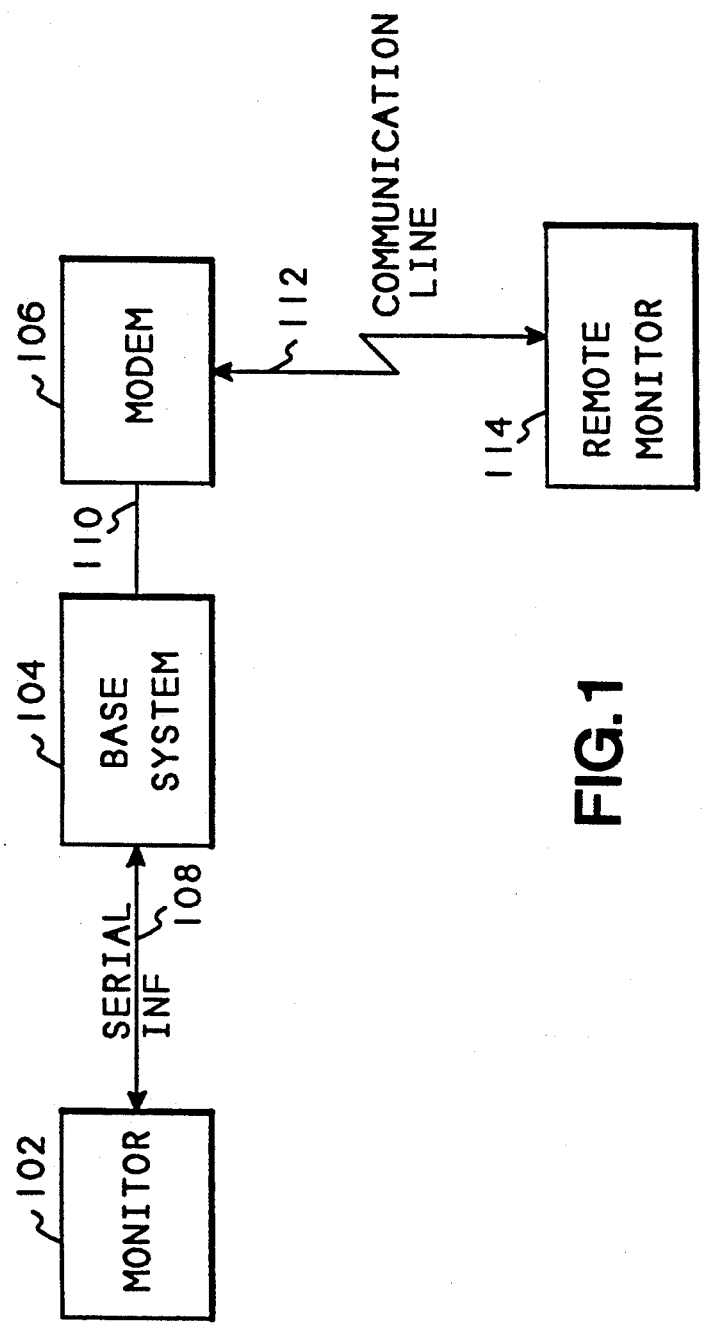
FIG. 1 shows a block diagram of the system of the present invention.

FIG. 1 shows a block diagram of the system of the present invention. Referring now to FIG. 1, a portable blood alcohol monitor 102 is attached to the subject being monitored. Periodically, typically once per day, the subject connects a serial interface 108 between the monitor 102 and a base system 104. When this connection is made, the monitor 102 transfers all the readings, tamper, error indicators, and other data, taken since the last connection into the base system 104 where they are stored. The base system 104 transmits these readings, at predetermined intervals, over a modem connection 110 to a modem 106 which sends the readings over a communications line 112 to a remote monitor 114. Typically, the communications line 112 is a telephone system. The portable blood alcohol monitor 102 analyzes the readings taken to determine whether the subject's blood alcohol content has exceeded a predetermined level. If the alcohol content of the subject's blood has exceeded a predetermined level, a record is stored for transmission to the remote monitoring station 114 which can notify a person in authority that a high measurement has been taken.

The base system 104 can be a device such as a personal computer, or it can be a device specifically designed to capture readings from the monitor 102 and transfer such readings to the remote monitoring station 114. In the preferred embodiment, the base system 104 is simply a store and forward device, and does not perform analysis of the readings taken by the monitor 102. In other embodiments of the invention, however, the base system 104 could be designed to perform such analysis and connect to the remote monitoring station 114 only if the subject's blood alcohol content exceeded a predetermined level or an error condition occurs. That is, while in the preferred embodiment the base system 104 simply stores the readings and transfers them to the remote monitoring station 114, the base system can monitor the readings and contact the remote monitoring station 114 when the readings exceeded predetermined levels or if there are any indications of a system malfunction, tampering, or a low battery condition.

Figure 2:
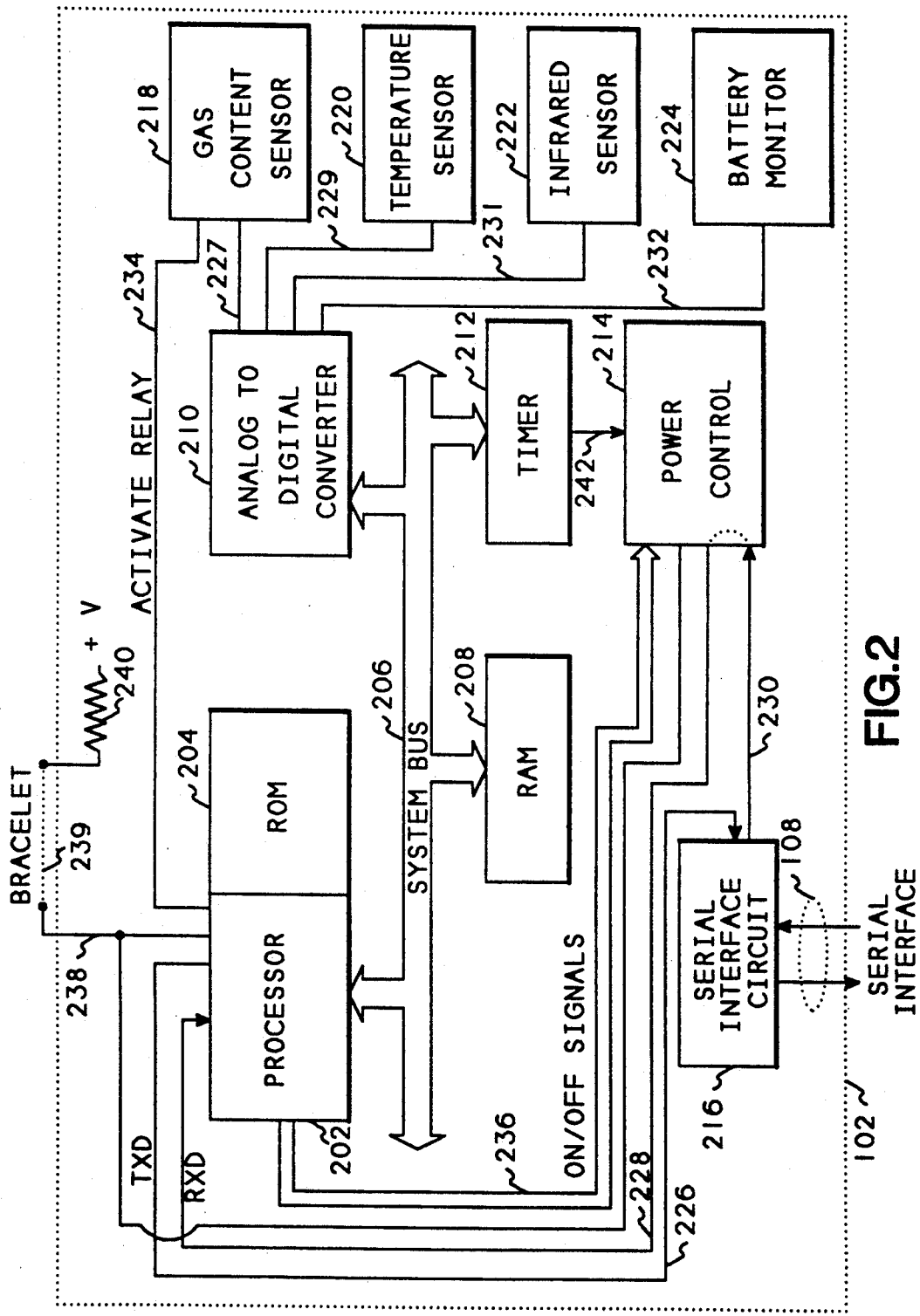
FIG. 2 shows a block diagram of the portable blood alcohol monitor of the system.

FIG. 2 shows a block diagram of the portable blood alcohol monitor 102 (FIG. 1). Referring now to FIG. 2, the monitor 102 contains a processor 202 which also contains read only memory, also called ROM, 204. The read only memory 204 is typically erasable, programmable read only memory, also called EPROM, which is built into the integrated circuit package that contains the processor 202. The software contained in this memory is a very basic program called a "boot strap" program. The boot strap program checks the validity of the main operating program contained in the random access memory (RAM) 208, establishes communication with a host computer system (not shown) or the base system 104 through the serial interface 108, and loads information, including the main operating program, into the monitor 102 through the serial interface 108.

The processor 202 communicates with other elements of the monitor 102 over a system bus 206. A random access memory 208, which is used to hold the main operating program and the data measurements taken by the monitor 102, is connected to the system bus 206. In operation, the program from the ROM 204 is used to start the monitor and then transfer control to the main operating program in the RAM 208 after verifying that the main operating program is correct, or after loading a new copy of the main operating program through the serial interface 108. Although operating the main program from the RAM 208 provides higher performance, the main program could also be operated from the ROM 204.

Also attached to the system bus 206 is an analog to digital converter 210 which receives signals via line 238 from the bracelet circuit 239. The analog to digital converter 210 converts data created by a gas content sensor 218, a temperature sensor 220, an infrared sensor 222, and a battery monitor 224. The information from the three sensors and battery monitor, are output as analog signals via lines 227, 229, 231 and 232, respectively which are connected to the analog to digital converter 210. The analog to digital converter 210 converts the analog signals into digital information which is input to the processor 202 over the system bus 206. After reading the information from the converter 210, the processor 202 stores the readings into the RAM 208. A block diagram of the gas content sensor 218 is shown below with respect to FIG. 3, and a block diagram of the temperature sensor 220 is shown below with respect to FIG. 4. The infrared sensor 222 is a specialized position sensitive detector integrated circuit, which is available as part number P2826, from Hamatsu Corp., Bridgewater, N.J., U.S.A. The battery monitor 224 has a voltage divider resistor network connected to the main system battery. The voltage divider outputs a signal which exceeds a logical "1" voltage when the battery is supplying a working voltage to the circuit, and outputs a logical "0" signal when the battery voltage has dropped below a usable working voltage.

A timer circuit 212 is also attached to the system bus 206. The processor 202 sends data to the timer 212 to cause it to time the intervals between alcohol samples. After the processor has sent information to the timer to cause it to delay the amount of time to the next reading, the processor sends an "off" signal over on/off signals 236 to a power control circuit 214 which causes the power control circuit 214 to remove power from the electronics of the system except for the timer 212 and the RAM 208. The RAM 208 has a separate backup battery which is always connected to the RAM 208.

After the time has expired, the timer 212 outputs a signal 242 to the power control circuit 214 which reactivates power to the processor and resets the processor to start processing for the next measurement. The process of controlling the timer 212, and the power control 214, as well as the process for performing an alcohol content reading, will be described below with respect to FIGS. 5 through 10.

The monitor 102 also contains a serial interface circuit 216 which allows communications over a serial interface 108 to the base system 104 (FIG. 1). The actual serial communications is controlled by the processor 202 by sending serial transmit data over signal 226 through the serial interface circuit 216 and out the serial interface 108. The serial interface circuit 216 merely converts the voltage level of the transmit data signal 226 into a level that is suitable for the serial interface 108. When serial data is input over serial interface 108 through the serial interface circuit 216, the input data is sent over signal 230 to the power control circuit 214. The signal loops through power control 214 and becomes the receive data signal 228 which is input to the processor 202. As the receive signal is passing through the power control circuit 214, it will cause the power control circuit 214 to supply power to the processor 202. Since the processor is normally not active between taking alcohol readings, the processor must be activated if the subject connects the monitor to the base system. This activation is performed by receiving serial data over the signal 230.

A signal 238 connects the processor 202 to a conductor 239 within a bracelet, which is used to attach the monitor to the human subject. The conductor 239 also connects to a pull-up resistor 240 which is connected to the main battery. If the subject breaks the conducting circuit 239 contained in the bracelet while trying to remove the monitor, the signal 238 will become inactive. This will cause the power control block 214 to supply power to the processor 202 which allows the processor 202 to immediately log the tamper error into RAM 208.

Figure 3:
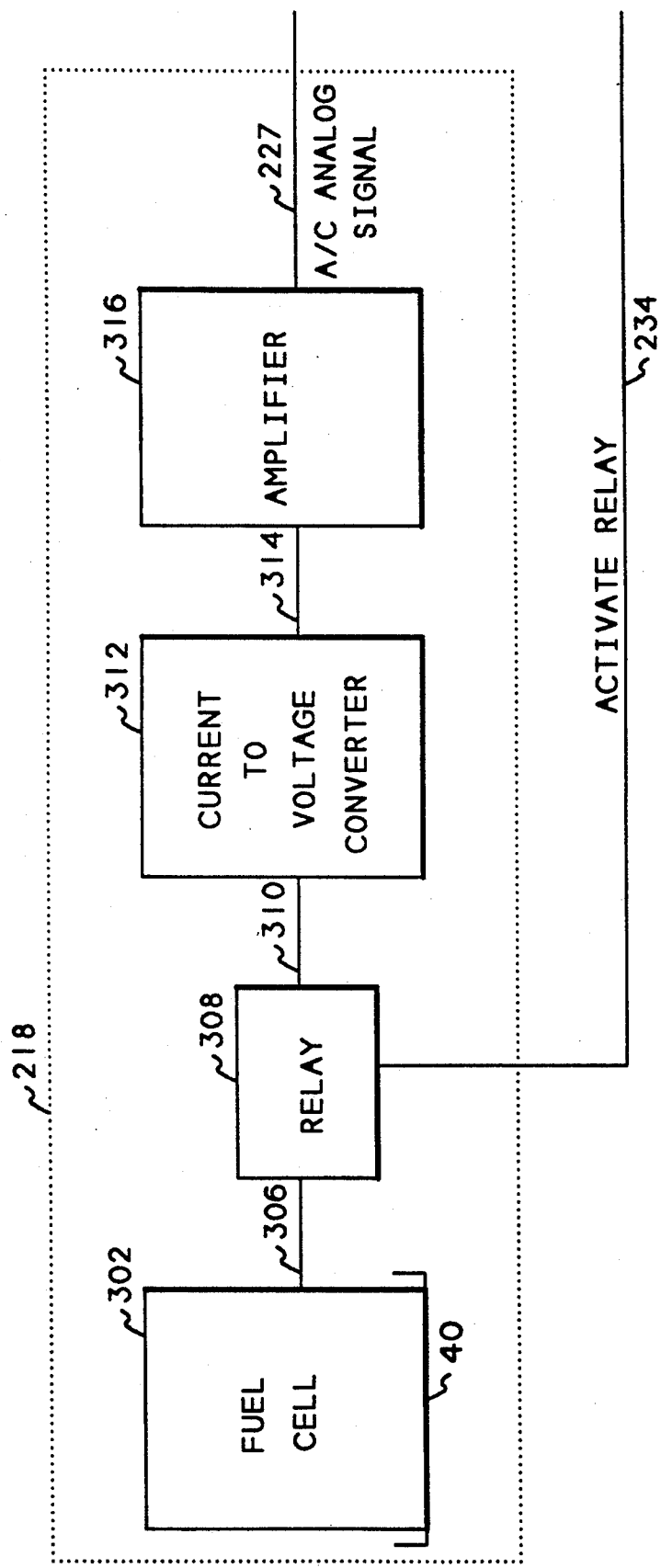
FIG. 3 shows a block diagram of the alcohol sensor of FIG. 2.

FIG. 3 shows a block diagram of the gas content sensor 218 of FIG. 2. Referring now to FIG. 3, the gas content sensor 218 contains a fuel cell 302 which is a model 7410 electro-chemical fuel cell available from Dräggerwerk, located at Lubeck, Germany. The fuel cell 302 contains an opening, called a sample port, to allow the air sample to enter the fuel cell. In order to ensure that the sample port contains the proper gases to be analyzed, an ethanol selective, non-hydrophilic membrane 304 is placed across the sample port of the fuel cell 302. This membrane improves the selectivity of the sensor to ethanol. The output 306 of the fuel cell 302 is an electrical current which is proportional to the amount of alcohol present in the air within the sample port. The sample port is placed at a predetermined distance, typically 1-5 millimeters, above the subject's skin. The sensor measures the amount of alcohol being emitted through the subject's skin thereby providing an indication of the subject's blood alcohol content. The output 306 is connected to a relay 308 which is activated by an ACTIVATE RELAY signal 234 output by the processor 202 (FIG. 2). As will be described below, the ACTIVATE RELAY signal causes a normally closed relay to be opened to remove a short from the fuel cell output terminals. This allows the output 306 to flow through to the signal 310 which is input to a current to voltage converter circuit 312. The output 314 of the current to voltage converter 312 is amplified by an amplifier 316 to become the alcohol content analog signal 226 which is connected to the analog to digital converter 210 (FIG. 2).

The relay 308 keeps the output of the fuel cell 302 shorted when the fuel cell is not being used to take a reading. When a reading is to be taken, the activate relay signal 234 causes the relay 308 to un-short the signal 306 which causes the fuel cell to start to provide voltage output by the sensor reacting to any alcohol present within the sample port. The output 226 is then monitored by the processor 202 for approximately 30 seconds, to determine if the fuel cell has sensed alcohol present within the sample port. This process will be more fully described below with respect to FIGS. 5 through 11.

Figure 4:
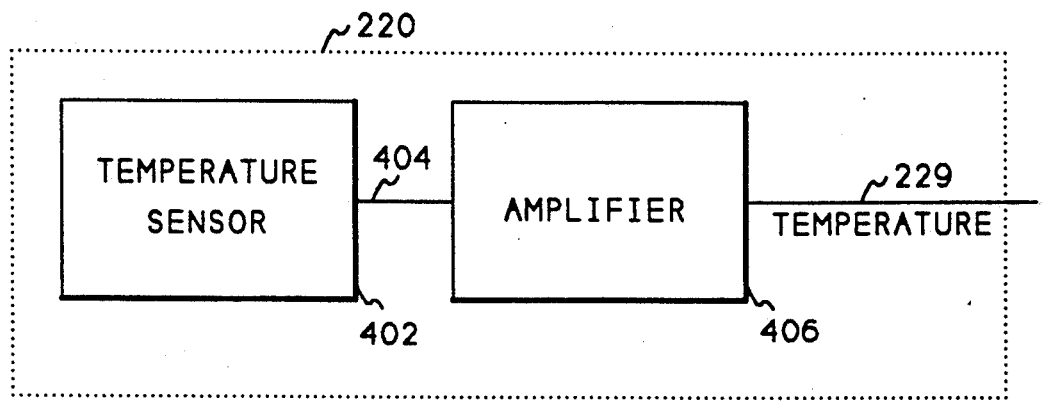
FIG. 4 shows a block diagram of the temperature sensor of FIG. 2.

FIG. 4 shows a block diagram of the temperature sensor circuit 220 of FIG. 2. Referring now to FIG. 4, the temperature sensor, circuit 220 contains a precision fahrenheit temperature sensor integrated circuit 402. This device is a model LM34 precision fahrenheit temperature sensor available from Digi-Key, located at Thief River Falls, Minn., U.S.A. The temperature sensor 402 provides a voltage output which increases linearly with an increase in temperature. The output 404 of the temperature sensor 402 is connected to an amplifier 406 which amplifies the signal to a level which can easily be converted by the analog digital converter circuit 210 (FIG. 2). The output 229 of the amplifier 406 is connected directly to the analog to digital converter circuit 210.

Figure 5:
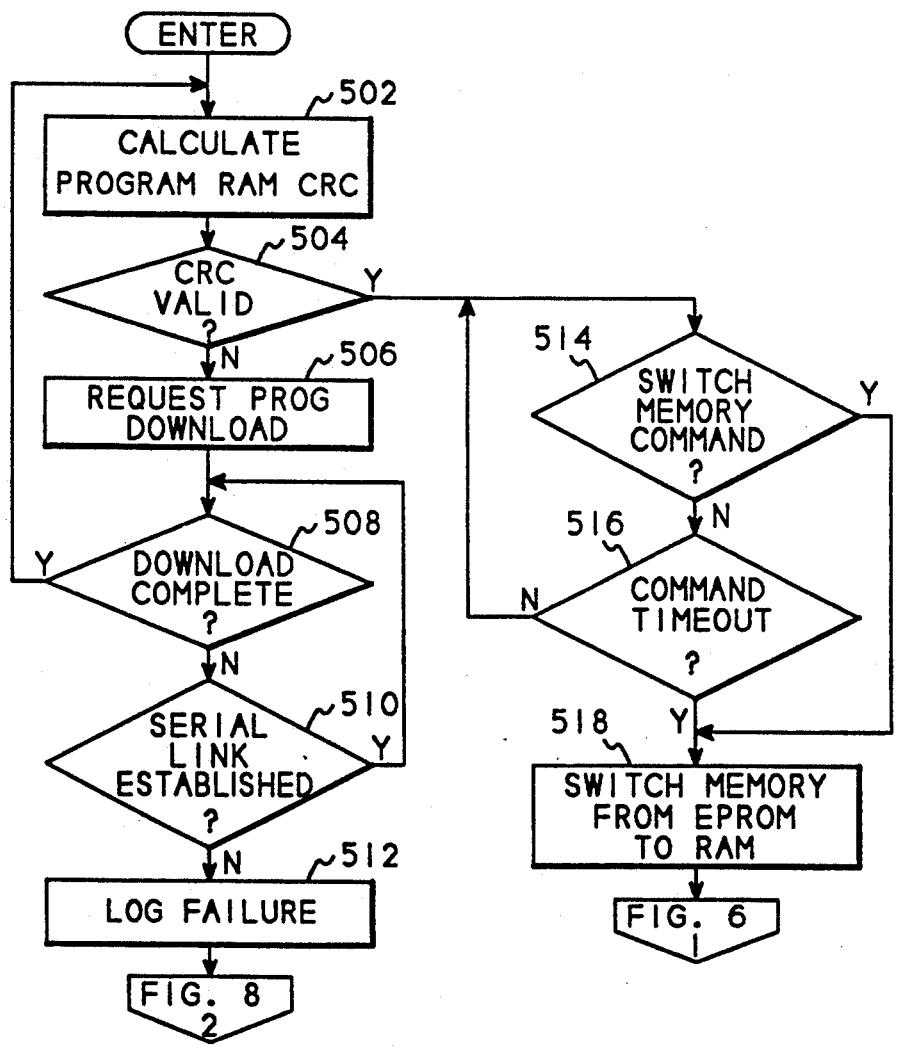
FIGS. 5 through 9 show a flowchart of the software contained in the invention.
Figure 6:
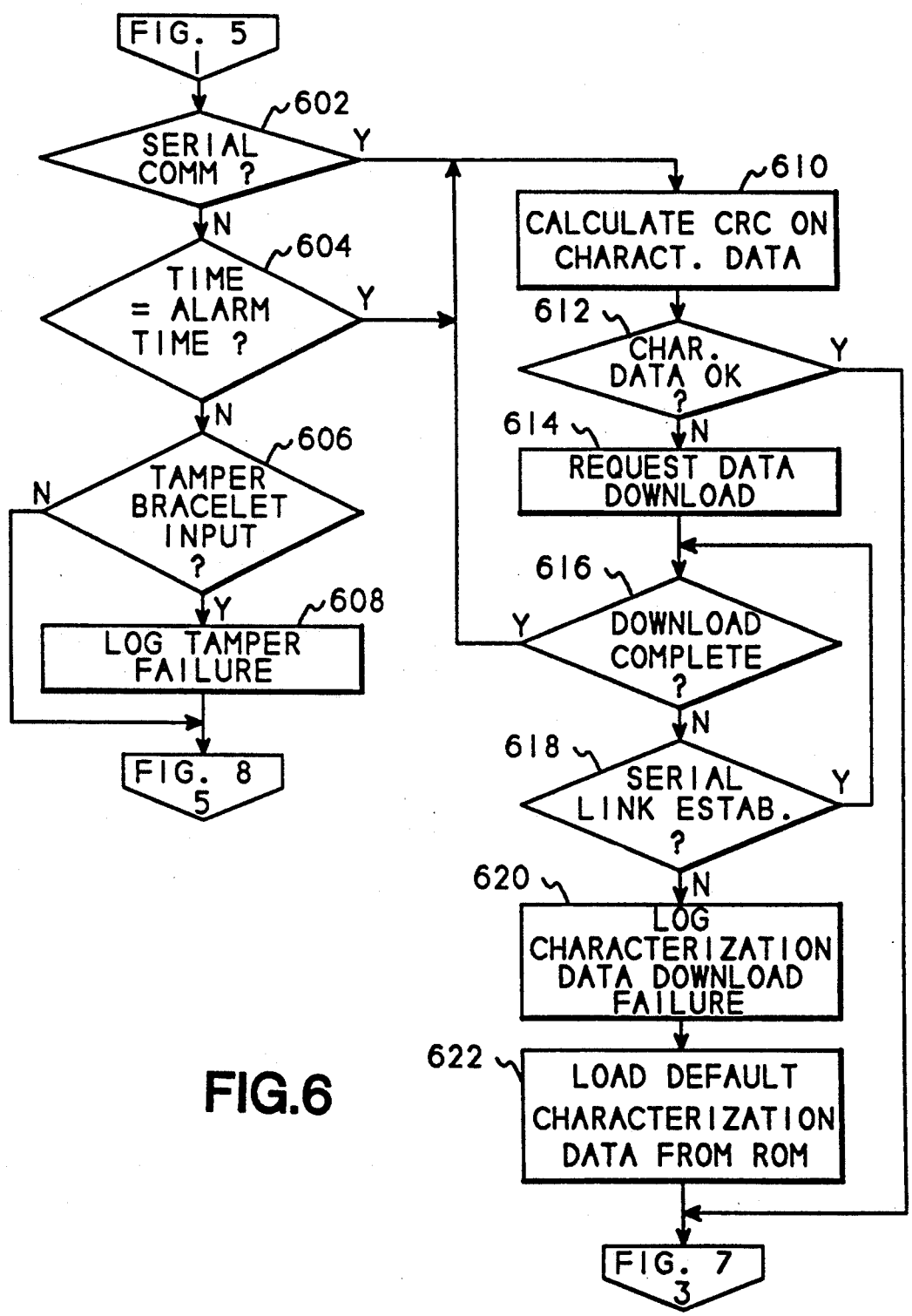
Figure 7:
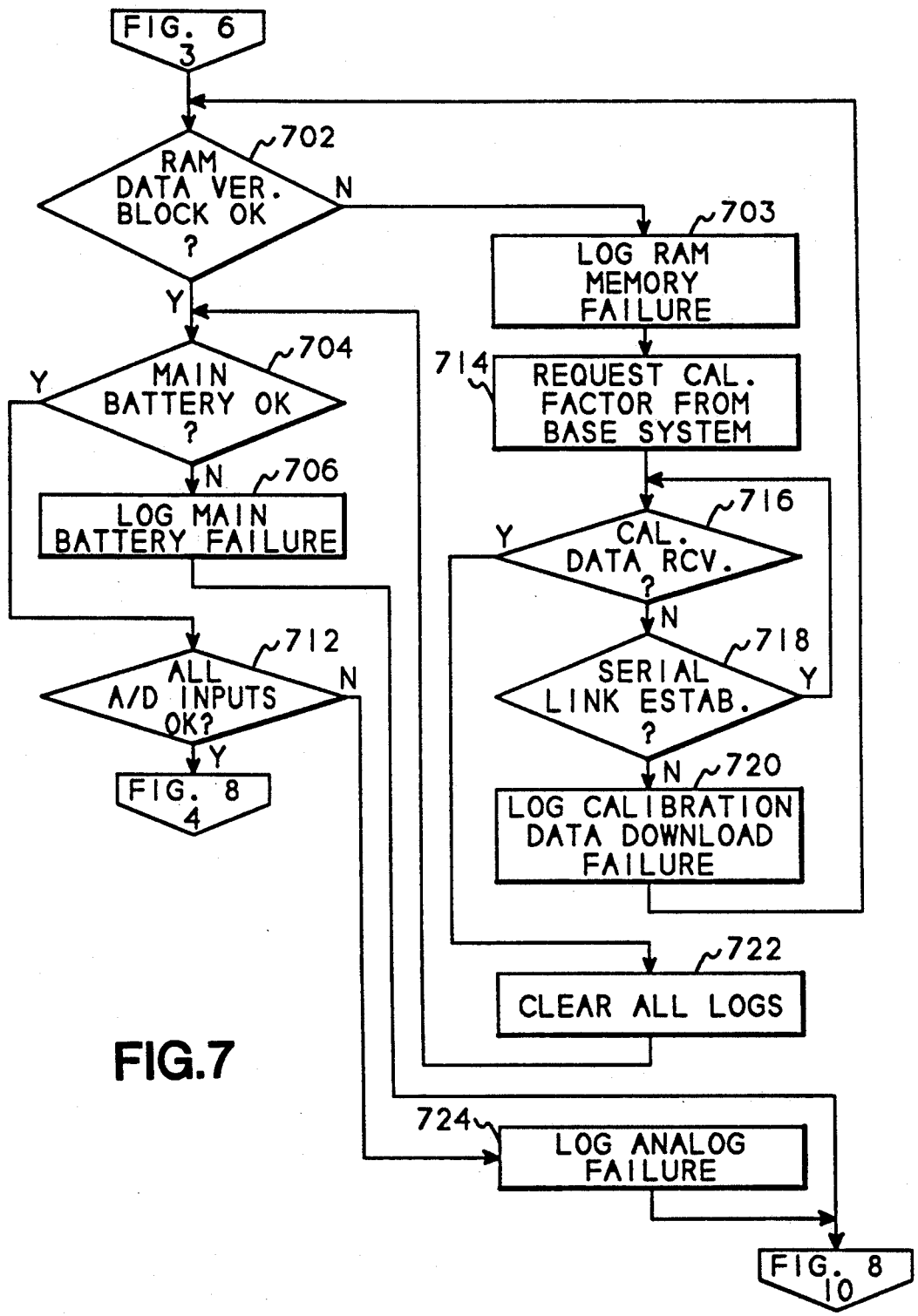

FIG. 5 shows a flowchart of the operation of the boot strap program which is contained in the ROM 204 (FIG. 2). FIGS. 6 through 11 show a flowchart of the software of the main operating program of the present invention. This software is loaded through the serial interface 108 from the base system 104 (FIG. 1) or from a host computer system (not shown), and stored in the RAM 208 (FIG. 2).

The software starts execution whenever the processor 202 is reset. This reset can occur from three different sources. When the timer set by the previous measurement process expires, it causes the power control circuit 214 to supply power to the processor 202 and at the same time to reset the processor 202 to start execution of the software. Also, if serial data is received over the serial interface 108, this data passes through the power control circuit 214 which also causes the processor to be reset. The bracelet monitoring input 238 can also reset the processor when a change in the voltage level being conducted by the bracelet circuit 239 is detected, indicating a tamper error.

Referring now to FIGS. 5 through 11, when the processor is reset, the software of FIG. 5 is entered. When the software first starts execution, block 502 calculates the cyclic redundancy information of the program stored in RAM 208 and determines whether the result indicates that the program was changed since it was loaded through the serial interface 108 into the RAM 208. Block 504 determines whether the CRC indicates that the program is valid.

If the program is not valid, block 504 transfers to block 506 which requests a new program download through the serial interface 108. Block 508 determines whether the download is complete and if not, control transfers to block 510 which determines whether the serial link has been established or is still established. If the serial link was not established or has dropped, block 510 transfers to block 512 which logs a program load failure and then transfers to FIG. 8 entry point number two to set a new timer value. If the serial link is still established, block 510 transfers back to block 508 until the download is complete. When the download is complete, block 508 transfers back to block 502 which recalculates the cyclic redundancy check information to check the new program code just loaded.

If the CRC is valid, thus indicating that the program code is intact, block 504 transfers to block 514 which determines whether a switch memory command has been received over the serial interface. If a switch memory command has been received, block 514 transfers to block 518. If a command has not been received, block 514 transfers to block 516 which determines whether the time to receive a command has expired. If the time has not expired, block 516 transfers back to block 514 and this loop continues until either a command is received or the time to receive a command has expired. After a command has been received or the time has expired, control transfers to block 518 which switches the program memory from the ROM 204 to the RAM 208 in order to execute the main operating system software. Control then transfers to FIG. 6 entry point one, and to block 602.

Block 602 determines whether the serial communications is active, and if it is not, block 602 transfers to block 604 which determines whether the timer expired, therefore, whether the software should take another alcohol measurement. If serial communications is not active and the timer has not expired, control transfers to block 606 which determines whether the tamper bracelet input is inactive. If the tamper bracelet input is inactive, control goes to block 608 which logs a tamper failure into the RAM 208. After logging the failure or if the tamper bracelet input was active, control transfers to FIG. 8 entry five to set a new timer value into the timer.

If the serial communications is active or the time had expired, control transfers to block 610 which calculates cyclic redundancy check information on characterization data stored within the RAM 208. The characterization data is data that was created by characterizing the fuel cell 302 (FIG. 3) and is used to adjust the readings obtained from the fuel cell to obtain a more accurate percentage of alcohol content.

Block 612 then determines whether the characterization data is intact, by determining whether the cyclic redundancy check information indicates an error. If the characterization data is not intact, that is, it has been modified in some manner, block 612 transfers to block 614 which requests a download of characterization data from the serial interface. Block 616 then determines if the download is complete and if not, transfers to block 618 which determines whether the serial link is still established. If the serial link is still established, block 618 transfers back to block 616 until the new characterization data has been downloaded and then control transfers back to block 610 to recalculate the cyclic redundancy check information. If the serial link has not been established or communication is broken during the transmission, control goes to block 620 which logs a data download failure into the RAM 208. Block 622 then loads default characterization data from the ROM 204 to use until new data can be downloaded. After loading default characterization data, or if the characterization data is intact and has not been modified, control transfers to FIG. 7 entry point three, and block 702.

Block 702 determines whether the RAM data verification block is intact. The RAM data verification block is data stored in the RAM 208 that is used to determine whether the contents of the data within the RAM 208 have been modified. If the RAM data verification block is not valid, indicating that the data has been modified, block 702 transfers to block 703 which logs a RAM memory failure. Control then goes to block 714 which requests calibration data from the base system 104. Block 716 then determines whether the calibration data has been received and if not, control goes to block 718 to determine whether the serial link has been established or is still established. If the link is still established, control transfers back to block 716 to loop until all the calibration data has been received. If the serial link is not established, control goes to block 720 which logs a calibration data download failure before transferring back to block 702. After the calibration data is received, block 716 transfers to block 722 which clears all log information within the RAM 208 and then transfers to block 704.

After clearing all log information or if the RAM data verification block is valid, control transfers to block 704 which samples the battery monitor 224 (FIG. 2), through the analog to digital converter 210 (FIG. 2), to determine whether the main battery is still supplying sufficient power. If the battery is not supplying sufficient power, control goes to block 706 which logs a main battery failure before transferring to FIG. 8 entry point 10 to turn off main power and place the system into standby mode.

Figure 8:
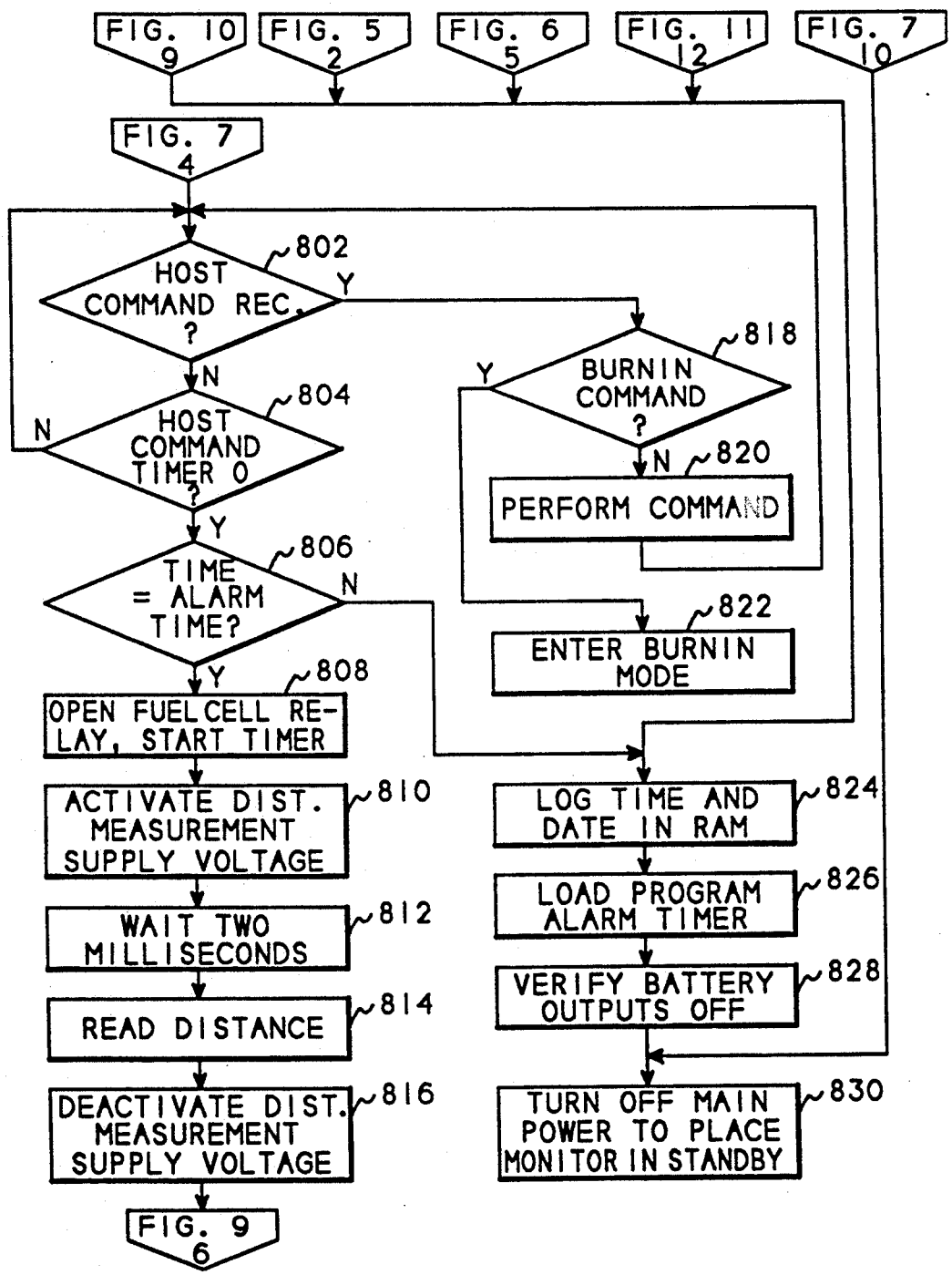
Figure 9:
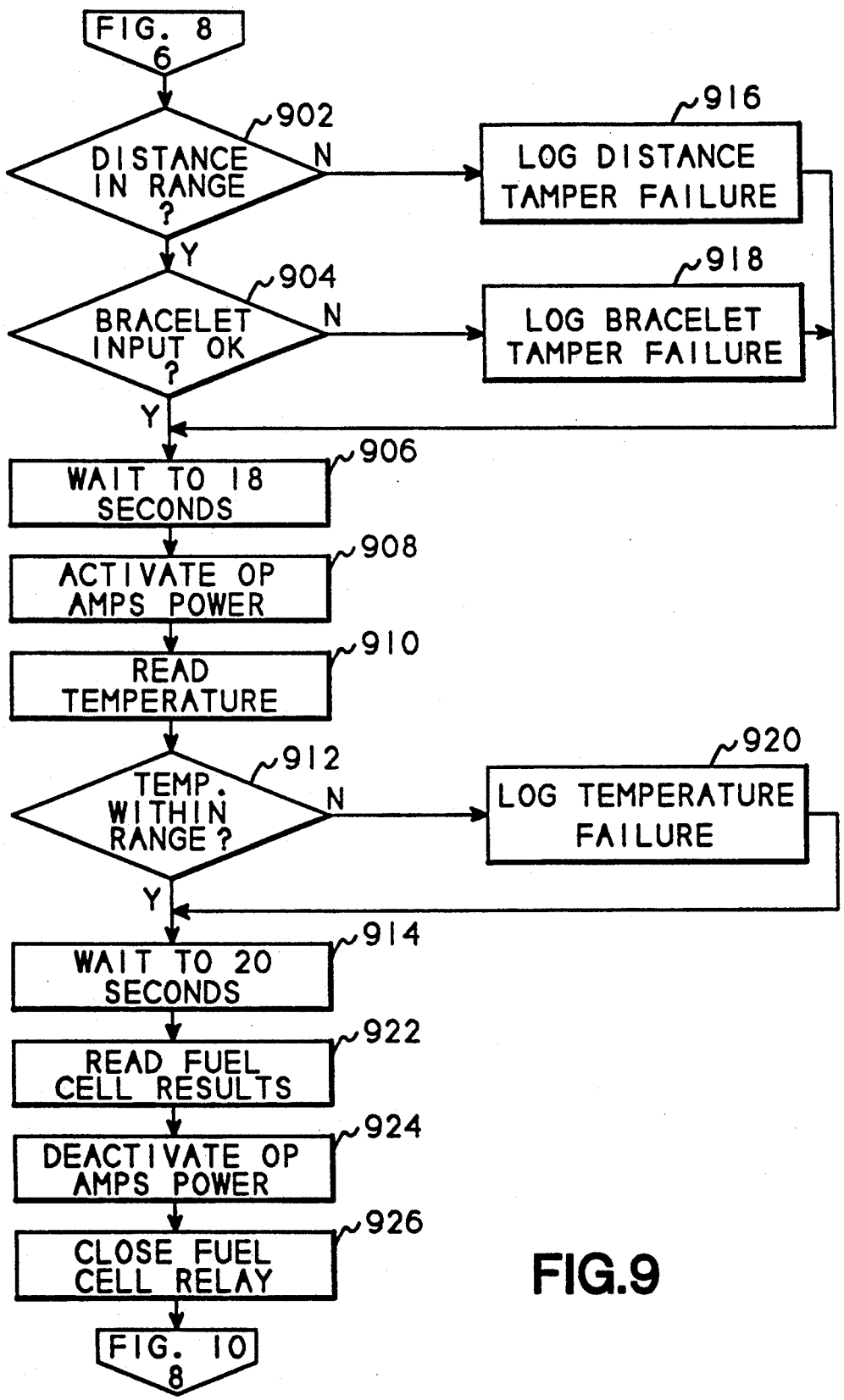
Figure 10:
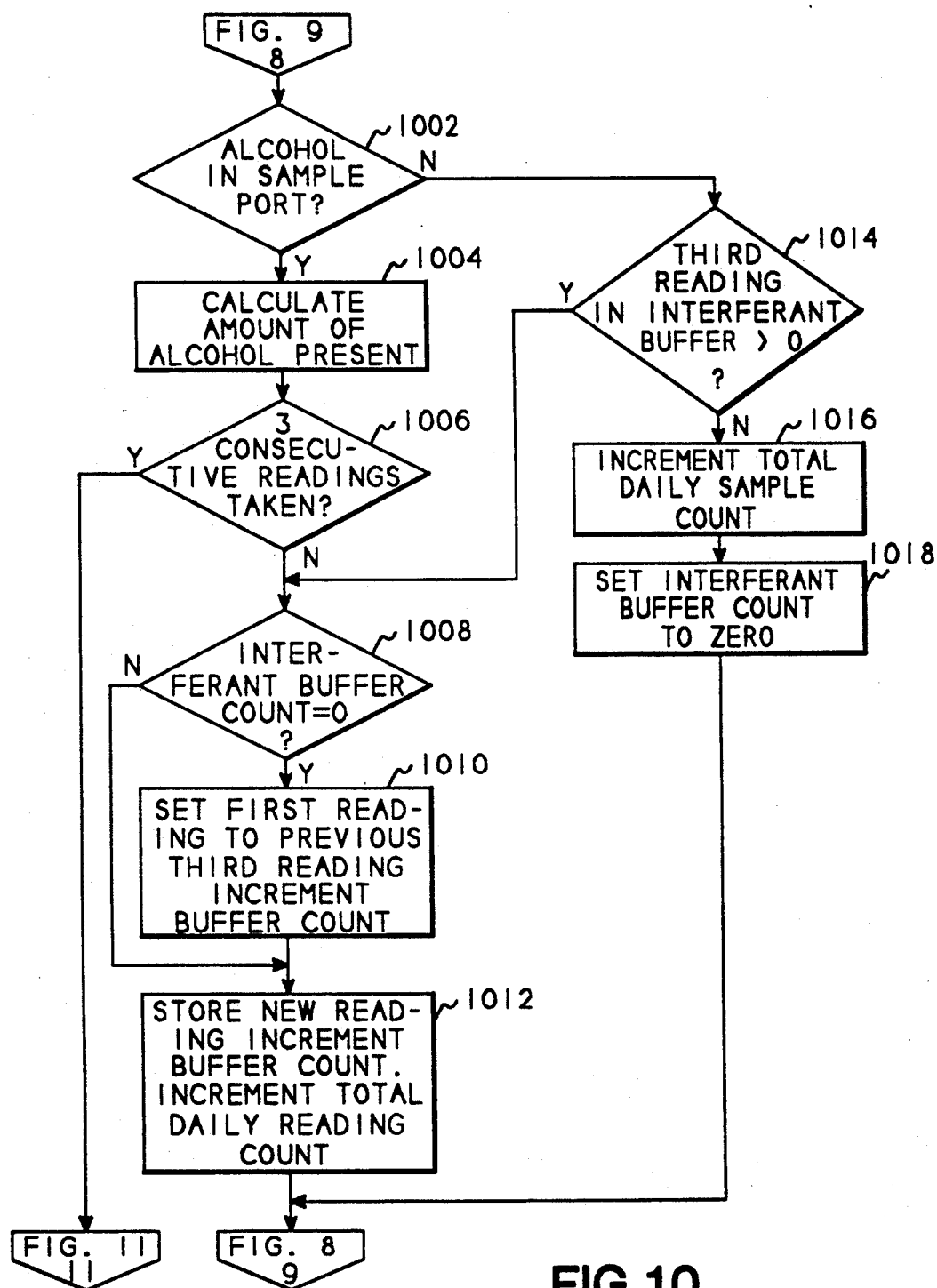
FIGS. 10 and 11 show a flowchart of the interferant detection process.

If the main battery is supplying an acceptable voltage, block 704 transfers to block 712 which determines whether all other analog to digital inputs are valid and if not, block 712 transfers to block 724 which logs an analog failure before transferring to FIG. 8 entry point 10 to shut down the system. If all analog inputs are valid, block 712 transfers to FIG. 8 block 802.

Block 802 determines whether a host command has been received from the base system 104 (FIG. 1), and if not, transfers control to block 804 which determines whether the time to receive a host command has expired. If the time has not expired, block 804 loops back to block 802 until either a host command is received or the wait time to receive a command has expired. If a host command is received, block 802 transfers to block 818 which determines whether the command received is a "burn-in" command. The burn-in command is used in initial manufacturing and testing of the unit, and if a burn-in command is received, block 818 transfers to block 822 which enters a test burn-in mode. The test burn-in mode puts the monitor unit into a slave configuration waiting to receive commands from the host computer system. The monitor can then be characterized. Characterization is the process of collecting the unit's sensor output voltage readings and storing these readings in RAM 208. The voltages are obtained under strictly controlled temperature conditions in an environmental chamber. A set of known alcohol standards is sampled by the monitor while in the chamber, and the resultant voltages are stored in RAM 208. The monitor remains in burn-in mode until the power is cycled or the monitor is reset.

If the command received is not a burn-in command, block 818 transfers to block 820 which performs the command before returning to block 802. The host commands performed by block 820 are 15 primarily commands related to diagnostics, such as diagnostic test, entering a slave mode for transferring programs back and forth between the monitor and the base system, auto-calibration diagnostics, transferring programs or transferring data. One of the host commands, however, is used to download the sample information which has been collected since the last download of this information to the host. That is, as each measurement is taken, a log is kept of the measurement and this log information is downloaded to the base system for eventual transfer to the remote monitor system.

If a host command is not received before the timer expires, control transfers to block 806 which determines whether the timer 212 expired. If the time set into the timer 212 has not expired, block 806 transfers control to block 824 which logs the time and date into the RAM 208. Block 826 then loads the timer 212 with the next "wake up" time for taking the next measurement. In a first embodiment of the invention, the time between measurements is set at 30 minutes. In another embodiment, however, the time between measurements can be set to a random time, to allow for random measurements. When random timing is used, the total number of measurements within a 24-hour period is still set to 48, the same number of measurements that is taken with a regular 30 minute cycle. This insures that the data area within the RAM 208 is not exceeded.

After programming the timer, block 828 verifies that all optional battery outputs have been turned off, to ensure that there is no excessive drain on the batteries, and then block 830 turns off main power to place the monitor device into standby until the timer 212 expires and restarts this cycle.

If the time has exceeded 30 minutes or the random time set in the last measurement cycle has expired, block 806 transfers to block 808 which opens the fuel cell relay and starts a timer. As discussed above with respect to FIG. 3, a relay 308 keeps the output of the fuel cell 302 shorted until a measurement is to be taken. When a measurement is to be taken, block 808 opens the fuel cell relay by sending the ACTIVATE RELAY signal 234 to the relay 308. After opening the fuel cell relay and setting the timer, block 808 transfers to block 810 which activates the infrared sensor 222 (FIG. 2) to take a distance measurement. This activation is accomplished by programming the power control circuit 214 to supply power to the infrared sensor 222. After activating the distance measurement sensor, block 812 waits two milliseconds and then block 814 reads the distance value from the infrared sensor 222. Block 816 then deactivates power to the distance measurement sensor to conserve battery power. Control then transfers to FIG. 9 entry point six and block 902.

Block 902 determines whether the distance measured in block 814 is within an acceptable range for the device being attached to the subject. A typical distance is 1-5 millimeters. If the distance is not within an acceptable range, block 902 transfers to block 916 which logs a distance tamper failure into the RAM 208 and then transfers to block 906.

If the distance is within range, block 902 transfers to block 904 which determines whether the bracelet input is valid. If the bracelet input is valid, the bracelet is still conducting and, therefore, has not been broken or removed from the subject. If the input bracelet indicates that it has been broken, block 904 transfers to block 918 which logs a bracelet tamper failure into the RAM 208.

Control then transfers to block 906 which waits 18 seconds for the system to settle before taking additional readings. Block 908 then activates OP amps power to the temperature sensors and the gas content sensors. Block 910 reads the temperature from the temperature sensor 220 and block 912 determines whether the temperature is within an acceptable range for being located next to the subject. A typical range for this sensor is 94 to 98 degrees fahrenheit. If the temperature is not within an acceptable range, block 912 transfers to block 920 which logs a temperature failure into the RAM 208. After logging the failure or if the temperature is within the range, control transfers to block 914 which waits an additional 20 seconds and then block 922 reads the fuel cell results from the gas content sensor 218 through the analog to digital converter 210. Block 924 deactivates the OP amps power to turn the temperature sensor and gas content sensor operational amplifiers off. Block 926 then deactivates the ACTIVATE RELAY signal 234 to close the fuel cell relay and prevent it from taking additional measurements. Control then goes to FIG. 10, block 1002.

Block 1002 determines if alcohol is present in the sample port. If alcohol is present, block 1002 transfers to block 1004 which calculates the amount of alcohol present. The amount of alcohol present is calculated by comparing a reading from the sensor 218 to the known readings in the characterization data to produce a base line blood alcohol result. This base line reading is then multiplied by the calibration factor which compensates for sensor drift from the time the characterization was performed. This result is further multiplied by a temperature coefficient to provide the final amount of blood alcohol present. Block 1006 then determines if three consecutive samples have been taken, and if not, transfers to block 1008. Block 1008 determines if the interferant buffer count is zero, indicating that this is the first sample taken. If the count is zero, block 1008 transfers to block 1110 which sets the first interferant buffer reading to the previous third buffer reading and increments the buffer count.

After setting up the interferant buffer, or if the count is not zero, control goes to block 1012 which stores the new sample data in the interferant buffer, and increments the count of readings as well as the daily reading count. Control then goes back to FIG. 8.

If no alcohol is in the sample port, block 1002 transfers to block 1014 which determines whether the third reading in the interferant buffer is greater than zero. If the buffer reading is greater than zero, block 1014 transfers to block 1008 to store the sample reading just taken.

If the buffer reading is not greater than zero, block 1014 goes to block 1016 which increments the total daily sample count. Then block 1018 sets the interferant buffer count to zero to reset the sampling process before transferring to FIG. 8.

Figure 11:
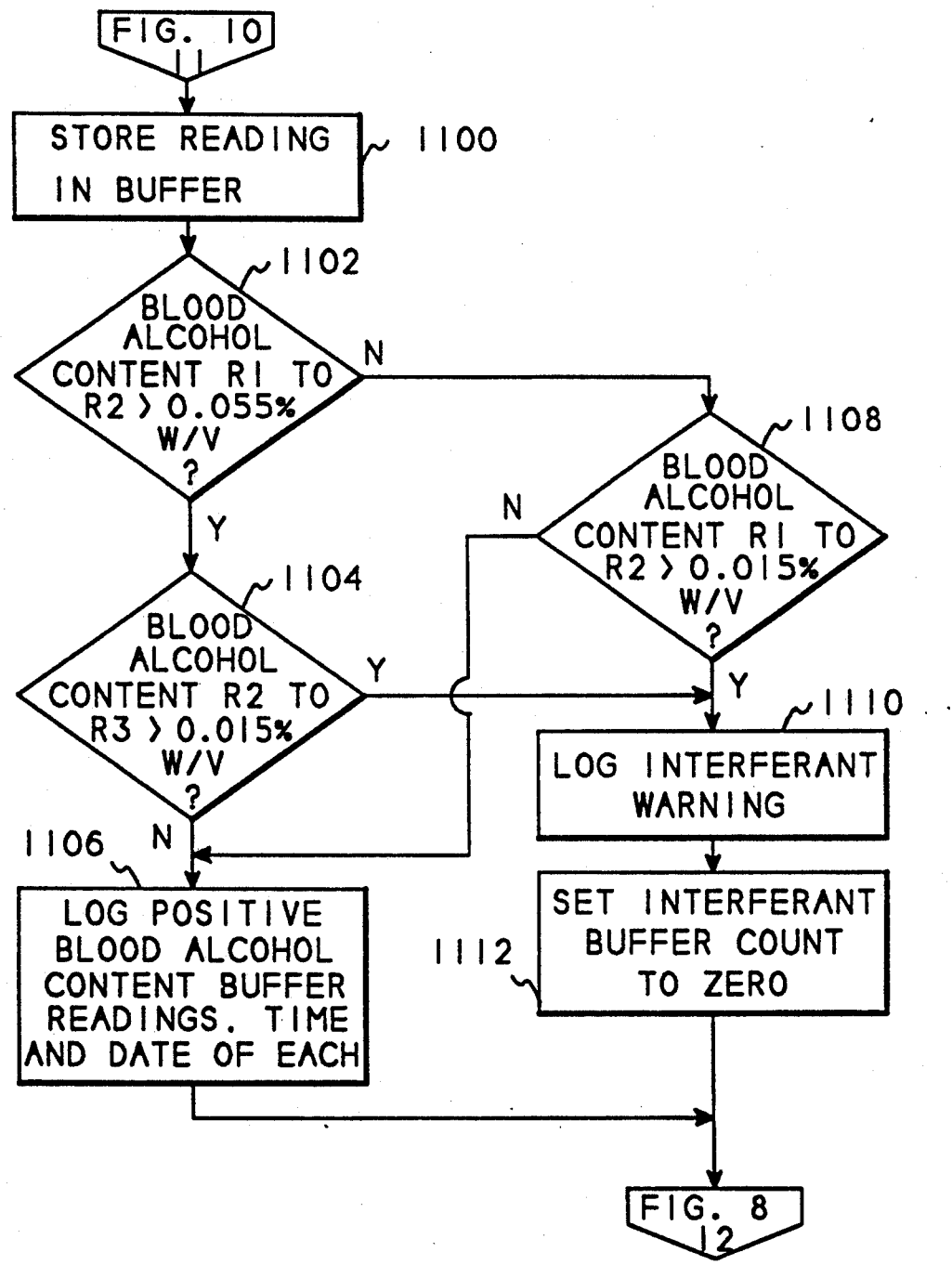

If three sample readings have been taken, block 1006 transfers to FIG. 11, block 1100 to evaluate the readings. Block 1100 stores the reading just taken, and block 1102 determines if the absorption rate in the blood alcohol content between the first and second readings is greater than 0.055% W/V. As described in "The Metabolism Rates of Alcohol in the Human Body" by Robert P. Shumate et al., *Journal of Forensic Medicine*, Volume 14, number 3, Jul.-Sep. 1967, if the absorption rate is greater than 0.055% W/V or if the burn off rate is greater than 0.015% W/V in a thirty minute period, the readings are not representative of alcohol content within a human body and must be due to an external source.

If the absorption rate is greater than 0.55% W/V, block 1102 transfers to block 1104 which determines if the burn-off rate between readings two and three is greater than 0.015% W/V. If this is not true, block 1104 goes to block 1106 to log the readings, including the date and time of each reading.

If block 1102 found that the burn-off rate was not greater than 0.055% W/V, it transfers to block 1108 which determines if the burn-off rate between readings two and three is greater than 0.015% W/V. If not, block 1108 transfers to block 1106 and log a positive reading.

If the burn-off rate is greater than 0.015% W/V, both blocks 1104 and 1108 transfer to block 1110 which logs an interferant warning into the RAM 208. Block 1212 then sets the interferant count back to zero before returning to FIG. 8.

Having thus described a presently preferred embodiment of the present invention, it will now be appreciated that the aspects of the invention have been fully achieved, and it will be understood by those skilled in the art that many changes in construction and circuitry and widely differing embodiments and applications of the invention will suggest themselves without departing from the spirit and scope of the present invention. The disclosures and the description herein are intended to be illustrative and are not in any sense limiting of the invention, more preferably defined in scope by the following claims.

What is claimed is:

1. A portable monitor for sensing blood alcohol levels in a human subject comprising:

alcohol measuring means for measuring a percentage of alcohol contained in a gas within a predetermined distance from the human subject's skin to create a percentage measurement;

timer means for activating said alcohol measuring means at predetermined time intervals to cause aid alcohol measuring means to create a plurality of percentage measurements at said predetermined time intervals;

storage means for storing said plurality of percentage measurements;

securing means for portably and securely attaching said measuring means to the human subject;

detection means for detecting when said blood alcohol monitor is removed form the human subject; and communication means for communicating said stored percentage measurements and detection results to a monitor station.

2. The portable blood alcohol monitor of claim 1 wherein said detection means comprises:

an electrical conductor within said securing means;

means for causing an electrical current to be conducted through said electrical conductor; and means for detecting an absence of electrical current in said electrical conductor.

3. The portable blood alcohol monitor of claim 1 wherein said detection means comprises:

distance measurement means for measuring the distance said blood alcohol monitor is located from the human subject;

means for detecting a predetermined excessive distance between said monitor and said human subject; and means for storing and transmitting to said monitor station an indication of excessive distance.

4. The portable blood alcohol monitor of claim 1 wherein said detection means comprises:

temperature measurement means for measuring the human subject's skin temperature at a predetermined distance from a point where said blood alcohol monitor is attached to the human subject;

means for detecting that said human subject's skin temperature is outside a predetermined range of temperatures; and means for storing and transmitting to said monitor station an indication of exceeding said range of temperatures.

5. The portable blood alcohol monitor of claim 1 wherein said communication means comprises serial data transmission means for sending said percentage of alcohol measurement and said detection results to said monitor station.

6. The portable blood alcohol monitor of claim 1 wherein said alcohol measurement means comprises a fuel cell.

7. The portable blood alcohol monitor of claim 1 wherein said timer means further comprises means for activating said alcohol measurement means at periodic intervals.

8. The portable blood alcohol monitor of claim 1 wherein said timer means further comprises means for activating said alcohol measurement means at random intervals.

9. The portable blood alcohol monitor of claim 1 wherein said communication means further comprises base system means for connecting to said blood alcohol monitor to retrieve said percentage of alcohol measured and said detection results for forwarding to said monitor station.

10. The portable blood alcohol monitor of claim 1 further comprising means for receiving data and machine instructions through said communication means.

11. The portable blood alcohol monitor of claim 10 wherein said machine instructions comprise operating software for said monitor.

12. The portable blood alcohol monitor of claim 1 wherein said alcohol measuring means further comprises means for determining that said percentage of alcohol exceeds a predetermined range and further wherein said communication means further comprises means for communicating said percentage of alcohol measured only when said percentage of alcohol measured exceeds a predetermined range of percentages.

13. The portable blood alcohol monitor of claim 12 wherein said alcohol measuring means further comprises means for determining that an interferant caused said predetermined range to be exceeded and further wherein said communication means further comprises means for sending an interferant indicator when said alcohol measurement means determines that an interferant caused said predetermined range to be exceeded.

14. A method for monitoring the percentage of blood alcohol content of a human subject, said method comprising the steps of:

(a) securely attaching an alcohol measurement device to the human subject using an attachment device;

(b) storing an error indication if the human subject tampers with said measurement device or an error occurs within said measurement device;

(c) measuring a percentage of alcohol expelled through the subject's skin into said measurement device and storing a measurement result;

(d) repeating steps (b) and (c) until a predetermined amount of time expires;

(e) transmitting each of said measurement results and each of said tamper and error indications to said monitoring station; and (f) repeating steps (b) through (e).

15. The method of claim 14 including the step of waiting a first predetermined amount of time prior to step (c), and storing an error indication according to step (b) during said first predetermined amount of time.

16. The method of claim 15 wherein said first predetermined amount of time is a variable time interval.

17. The method of claim 14 wherein step (b) further comprises the steps of:

(b1) determining if a temperature measurement of the human subject's skin is within a predetermined range of temperatures; and (b2) if said temperature is outside said predetermined range, sending said error indication.

18. The method of claim 14 wherein step (b) further comprises the steps of:

(b1) measuring a distance between said measurement device and the human subject's skin; and (b2) if said distance is outside a predetermined range, sending said error indication.

19. The method of claim 14 wherein step (c) further comprises the step of:

(c1) if a change in said percentage of alcohol exceeds a predetermined increase rate during a predetermined time period, storing an interferant indication.

20. The method of claim 19 wherein step (c) further comprises the step of:

(c2) transmitting said interferant indication to said monitor station.

21. The method of claim 14 wherein step (c) further comprises the step of:

(c1) if a change in said percentage of alcohol exceeds a predetermined decrease rate during a predetermined time period, storing an interferant indication.

22. The method of claim 21 wherein step (c) further comprises the step of:

(c2) transmitting said interferent indication to said monitor station.

23. The method of claim 14 wherein step (d) further comprises the step of:

(d1) transmitting any diagnostic errors to said monitor station.

24. A portable monitor for sensing blood alcohol levels in a human subject comprising:

alcohol measuring means for measuring a percentage of alcohol contained in a gas within a predetermined distance form the human subject to create a percentage measurement;

timer means for activating said alcohol measuring means at predetermined time intervals to cause said alcohol measuring means to create a plurality of percentage measurements at said predetermined time intervals;

storage means for storing said plurality of percentage measurements; and securing means for securing said alcohol measuring means within a selected distance from the human subject's skin.

25. A portable monitor according to claim 24, wherein detection means is provided for detecting when said alcohol measuring means is greater than the selected distance from the human subject.

26. A portable monitor according to claim 24, wherein communication means is provided for communicating said stored percentage measurements and distance measurements to another monitor.

27. A portable monitor according to claim 26, wherein a means is provided at said other monitor to receive said percentage measurements and distance measurements from said communication means.

* * * * *

UNITED STATES PATENT AND TRADEMARK OFFICE
Certificate

Patent No. 5,220,919                                                    Patented: June 22, 1993

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Mary F. Phillips, Lakewood, CO (US); Jeffrey S. Hawthorne, Aurora, CO; and Brian Kirby Phillips, Lakewood, CO (US).

Signed and Sealed this Twenty-seventh Day of October 2009.

<div style="text-align:right">

BRIAN L. CASLER
*Supervisory Patent Examiner*
Art Unit 3737

</div>